(12) United States Patent
Cheung

(10) Patent No.: US 8,153,436 B2
(45) Date of Patent: Apr. 10, 2012

(54) ASSAYS FOR DISEASE-ASSOCIATED CRYSTALS IN BIOLOGICAL SAMPLES

(75) Inventor: Herman S. Cheung, Miami, FL (US)

(73) Assignees: The United States of America as represented by the Department of Veterans Affairs, Washington, DC (US); University of Miami, Miami, FL (US)

( * ) Notice: Subject to any disclaimer, the term of this patent is extended or adjusted under 35 U.S.C. 154(b) by 268 days.

(21) Appl. No.: 12/031,689

(22) Filed: Feb. 14, 2008

(65) Prior Publication Data

US 2008/0194042 A1 Aug. 14, 2008

Related U.S. Application Data

(60) Provisional application No. 60/901,713, filed on Feb. 14, 2007.

(51) Int. Cl.
*G01N 33/20* (2006.01)
*G01N 33/60* (2006.01)
*C12Q 1/00* (2006.01)
*C12Q 1/34* (2006.01)
*C12Q 1/42* (2006.01)

(52) U.S. Cl. .......... 436/79; 435/4; 435/18; 435/21; 436/57

(58) Field of Classification Search .......... 435/4, 18, 435/21
See application file for complete search history.

(56) References Cited

U.S. PATENT DOCUMENTS 5,776,348 A * 7/1998 Selengut et al. ............ 210/698
6,413,778 B1 * 7/2002 Carpenter et al. ............ 436/4

OTHER PUBLICATIONS

Proia et al., "Identification of calcium oxalate crystals using alizarin red S stain" Archives of pathology & laboratory medicine, (Feb. 1985) vol. 109, No. 2, pp. 186-189.*
Cheung et al, "Inhibition of CPPD crystal formation in articular cartilage vesicles and cartilage by phosphocitrate," *J. Biol. Chem.* 271(45):28082-28085 (1996).
Cheung et al, "Phosphocitrate blocks nitric oxide-induced calcification of cartilage and chondrocyte-derived apoptotic bodies," *Osteoarthritis and Cartilage* 7(4):409-412 (1999).
Dalal et al, "Molecular dynamics simulation studies of the effect of phosphocitrate on crystal-induced membranolysis," *Biophys. J.* 89(30):2251-2257 (2005).
Nair et al, "Phosphocitrate inhibits a basic calcium phosphate and calcium pyrophosphate dihydrate crystal-induced mitogen-activated protein kinase cascade signal transduction pathway," *J. Biol. Chem.* 272(30):18920-18925 (1997).
Rosenthal, "Update in calcium deposition diseases," *Curr. Opin. Rheumatol.* 19(2):158-162 (2007).
Sallis et al, "Inhibitors of articular calcium crystals," *Curr. Opin. Rheumatol.* 15(3):321-325 (2003).
Wierzbicki et al, "Molecular modeling of inhibition of crystals of calcium pyrophosphate dihydrate by phosphocitrate," *J. Molecular Structure (Theochem)* 454(2):287-297 (1998).
Wierzbicki et al, "Molecular modeling of inhibition of hydroxyapatite crystal by phosphocitrate," *J. Molecular Structure (Theochem)* 529(1-3):73-82 (2000).
Wierzbicki et al, "Molecular dynamics simulation of crystal induced membranolysis," *J. Phys. Chem. B* 107(44):12346-12351 (2003).
Chen et al., "Synovial Fluid Analysis for Identification of Crystals," cited in *Crystal-Induced Arthropathies: Gout, Pseudogout and Apatite-Associated Syndromes*, edited Wortmann et al., Taylor & Francis, Inc., New York, NY Ch. 9:157-168 (2006).
Cheung, "Therapeutic Strategies for Calcium-Containing Crystal Arthropathies," cited in *Crystal-Induced Arthropathies: Gout, Pseudogout and Apatite-Associated Syndromes*, edited Wortmann et al., Taylor & Francis, Inc., New York, NY Ch. 9:157-168 (2006).
Cheung et al., "Phosphocitrate Blocks Calcification-Induced Articular Joint Degeneration in a Guinea Pig Model," *Arthritis Rheum.* 54(8):2452-2461 (2006).
Halverson, "Other Methods of Crystal Identification," cited in *Crystal-Induced Arthropathies: Gout, Pseudogout and Apatite-Associated Syndromes*, edited Wortmann et al., Taylor & Francis, Inc., New York, NY Ch. 9:157-168 (2006).

* cited by examiner

*Primary Examiner* — Mark Shibuya
*Assistant Examiner* — Christine Foster
(74) *Attorney, Agent, or Firm* — Acuity Law Group, P.C.; Daniel M. Chambers

(57) ABSTRACT

Methods of assaying for disease-associated crystal species in biological samples are described. Such methods involve contacting a patient sample with an excess of a detectable crystal-tagging compound reactive with a plurality of crystal species under conditions that allow the detectable crystal-tagging compound to react with a plurality of crystal species, if present, to form tagged crystal species complexes. Substantially all unreacted tagging compound is then removed. If desired, chemical, enzymatic, or physical treatment can be used to selectively degrade some, but not, of the tagged crystal species. Assessment of soluble versus crystal-associated label is then performed.

6 Claims, No Drawings

ASSAYS FOR DISEASE-ASSOCIATED CRYSTALS IN BIOLOGICAL SAMPLES

RELATED APPLICATION

This application claims the benefit of and priority to provisional application Ser. No. 60/901,713, filed on Feb. 14, 2007, the contents of which are herein incorporated by reference in their entirety for any and all purposes.

GOVERNMENT RIGHTS

This invention was made with U.S. government support under National Institutes of Health grant no. R01-AR 38421-15. The U.S. government may have certain rights in this invention.

TECHNICAL FIELD

The present invention relates to assays for disease-associated crystal species in biological samples.

BACKGROUND OF THE INVENTION

1. Introduction

The following description includes information that may be useful in understanding the present invention. It is not an admission that any of the information provided herein, or any publication specifically or implicitly referenced herein, is prior art, or even particularly relevant, to the presently claimed invention.

2. Background

The multiplicity and diversity of roles for mineral elements ensures that essential metabolic reactions are maintained for an organism's life cycle. The importance of calcium, for example, is exemplified by its essentiality not only to the development and maintenance of the skeleton, but also by its role in specific enzyme activation and other biochemical and physiological parameters.

Deposition of mineral salts (e.g., calcium salts) can be triggered by tissue trauma or other signals such as abnormal fluctuations in intracellular calcium ion concentrations. Accordingly, detection and analysis of calcium crystal species, as well as other crystal species, could be important in diagnosing and managing various diseases.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "antibody" herein is used in the broadest sense and specifically covers monoclonal antibodies (including full length monoclonal antibodies), polyclonal antibodies, multispecific antibodies (e.g., bispecific antibodies), antibody fragments, chimeric antibodies, and binding agents that employ the CDRs (or variant thereof that retain antigen binding activity) of the parent antibody. Antibodies retain at least one desired activity of the parent antibody. Desired activities can include the ability to bind the antigen, or epitope-containing peptide, specifically. "Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

"Basic calcium phosphate" or "BCP" refers to carbonate-substitute apatite, octacalcium phosphate, and tricalcium phosphate.

A "biological sample" refers to a sample taken from a patient or subject. Such samples include tissue samples and fluid samples. A "fluid sample" includes a sample of a patient's blood, plasma, serum, urine, cerebrospinal fluid, lymph, synovial fluid, bile, semen, saliva, tears, and aqueous or vitreous humor.

A "label" refers to a detectable compound or composition that is conjugated directly or indirectly to another molecule to allow detection. The label may itself be detectable (e.g., radioisotope labels or fluorescent labels) or, in the case of an enzymatic label, may catalyze chemical alteration of a substrate compound or composition that is detectable. A label may also be a ligand for another molecule, such as one member of a high affinity binding pair (e.g., a ligand and its receptor, an antigen (or antigenic peptide) and an antibody specifically reactive against the antigen, biotin and avidin, etc.).

"Mammal" for purposes of treatment refers to any animal classified as a mammal, including humans, domestic and farm animals, and zoo, sports, or pet animals, such as dogs, horses, cats, cows, etc.

A "patentable" composition, process, machine, or article of manufacture means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

A "plurality" means more than one.

The terms "separated", "purified", "isolated", and the like mean that one or more components of a sample are or have been physically removed from, or diluted in the presence of, one or more other sample components. Sample components that may be removed or diluted during a separating or purifying step include, chemical reaction products, unreacted chemicals, proteins, carbohydrates, lipids, and unbound molecules.

By "solid phase" is meant a non-aqueous matrix to which a binding reagent can adhere. Examples of solid phases include those formed partially or entirely of glass (e.g. controlled pore glass), polysaccharides (e.g., agarose), polyacrylamides, polystyrene, polyvinyl alcohol, and silicones. In certain embodiments, depending on the context, the solid phase can comprise the well of an assay plate, a portion of a diagnostic device, etc.

The term "species" refers to a population of chemically indistinct molecules.

"Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

A "subject" or "patient" refers to an animal known to have or suspected of having a disease, disorder, or injury in need of diagnosis and/or treatment. Animals include vertebrates, with mammals such as bovine, canine, equine, feline, ovine, porcine, and primate (including humans and non-humans primates) animals being particularly preferred examples.

The methods and kits of the invention are useful in diagnosis and treatment. "Therapy" refers to the prevention and/or treatment of diseases, disorders, or physical trauma. The term "therapeutic" encompasses the full spectrum of treatments for a disease, disorder, or injury. A "therapeutic" agent may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

"Treatment" refers to both therapeutic treatment and prophylactic or preventative measures. Those in need of treatment include those already with the disorder as well as those in which the disorder is to be prevented.

SUMMARY OF THE INVENTION

This object of this invention is to provide patentable methods, reagents, and kits to assay for one or more for disease-associated crystal species in biological samples. Such assays can be used for diagnostic purposes, including to monitor disease progression and therapeutic efficacy, and they can be is qualitative, semi-quantitative, or quantitative.

Thus, one aspect of the invention concerns methods for performing such assays. In general, such methods involve contacting a biological sample from a patient with an excess of a detectable crystal-tagging compound reactive with a plurality of crystal species under conditions that allow the detectable crystal-tagging compound to react with a plurality of crystal species if present in the biological sample to form tagged crystal species complexes. Excess detectable crystal-tagging compound is then removed and the tagged crystal species complexes detected.

In preferred embodiments, the biological sample is a fluid sample, such as synovial fluid. Preferred detectable crystal-tagging compounds are those that comprise a crystal reactive compound (e.g., an anti-mineralization compound such as phosphocitrate, which reacts with calcium-containing crystals) and a detectable label. Preferred labeling moieties (i.e., "labels") include radiolabels (e.g., $^{111}$In, $^{99}$Tc, $^{14}$C, $^{131}$I, $^{125}$I, $^{3}$H, $^{32}$P, or $^{35}$S), fluorescent labels, and members of high affinity binding pairs (e.g., antibody-antigen, receptor-ligand, biotin-avidin, etc.).

In preferred embodiments, the disease-associated crystal species is a crystallized basic calcium phosphate species (e.g., carbonate-substituted apatite, octacalcium phosphate, and tricalcium phosphate), crystallized calcium pyrophosphate dihydrate, crystallized magnesium-substituted tricalcium phosphate, crystallized calcium oxalate, or a combination of these crystal species. Calcium-containing crystal species are implicated in various diseases, including osteoarthritis (OA), pseudogout, and acute calcific periarthritis.

In some embodiments, the detectable crystallized calcium complexes are contacted with a chemical or enzymatic reagent (e.g., a pyrophosphorylase) that selectively degrades some but not all of the different crystallized calcium species (e.g., crystallized calcium pyrophosphate dihydrate but not crystallized basic calcium phosphate species) so as to release a soluble detectable species into solution for subsequent detection.

Another aspect concerns kits for performing the assays of the invention. Typically, such kits include a detectable crystal-tagging compound that reacts with a plurality of disease-associated crystal species, as well as a reagent that selectively degrades at least one of the crystallized disease-associated crystal species reactive with the detectable crystal-tagging compound. In preferred embodiments, the detectable crystal-tagging compound (e.g., phosphocitrate labeled with a radio-label or fluorescent label) and selective degradation reagent (e.g., a pyrophosphorylase) are stored separately, for example, in different vials, and are provided to users in a package. Instructions for use, such a show to perform the particular assay, are preferably also included within the package.

A related aspect concerns devices configured to perform an assay according to the invention. Preferably, such devices employ a solid phase, and include devices configures to perform competitive and/or sandwich immunoassays.

Yet another aspect concerns applications for the assays of the invention, such as for diagnostic purposes, including to monitor disease progression and therapeutic efficacy. As will be appreciated, the assays of the invention can performed in a qualitative, semi-quantitative, or quantitative manner.

The foregoing and other aspects of the invention will become more apparent from the following detailed description and claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Crystal identification is an important diagnostic tool to identify various crystal-deposition diseases. The concentration of crystals in the synovial fluid in joints of the patients can be used as to determine whether a patient has a crystal-deposition disease, disorder, or injury or a marker for the severity of the disease. Conversely, such assays can be used to assess of the success or failure of a clinical treatment of the disease.

A variety of mineral salts can be deposited as crystals in biological systems. Sometimes, such deposition is aberrant and results from or is indicative of a disease, disorder, or injury (i.e., is "disease-associated"). For example, calcification in soft tissues in articular joints such as the knees is often associated with degenerative joint disease such as osteoarthritis. These calcified deposits are made up insoluble calcium salts of various formulations. Each form of calcium salt can cause chronic problems as well as dramatic inflammatory episodes.

While the instant invention is generally described in connection with disease-associated calcium crystals, those in the art will appreciate that the invention can readily be adapted for practice with other disease-associated crystal species.

Initially, calcium may accumulate in an amorphous state, but under certain conditions it can nucleate and transform into any of several hard, crystalline salts having minimum solubility. In some cases, such crystalline salts, if they persist, can activate further events and lead to the development of a specific pathological disease state. Indeed, this scenario prevails in a broad range of diseases, including renal calcinosis, urinary lithiasis, arteriosclerosis, heart valve calcification, soft tissue and tumor calcification, chondrocalcinosis, and in selected arthropathies.

The deposition of calcium-containing crystals, including basic calcium phosphate (BCP), calcium pyrophosphate dihydrate (CPPD), magnesium-substituted tricalcium phosphate (Whitlockite), and calcium oxalate crystals in articular tissues is an under-recognized disease-related event. These crystals precipitate in the extracellular matrix of the cartilage and can release into articular joint space. Calcium crystals occur frequently in osteoarthritis (OA) joints, and each may be phlogistic. CPPD crystals can cause acute attacks of pseudogout, while BCP crystals can cause acute calcific periarthritis. Clinical observations indicate that exaggerated and uniquely distributed cartilage degeneration is associated with these deposits, and they may magnify the degenerative process.

Synovial Fluid Analysis and Crystal Identification

The synovium is the tissue lining the joint space. It contains the synovia and terminates at the margin of the articular cartilage. Synovial fluid is a dialysate of blood plasma into which hyaluronate, a glycoaminoglycan of high molecular weight, is secreted by the synoviocytes. Synovial fluids may be obtained readily from the larger joints by any suitable method, including arthrocentesis. Gross, microscopic, and laboratory analyses of the synovial fluids have gained information about various arthritic diseases and systemic rheumatic diseases with prominent joint involvement. The presence of crystals in joint fluid is an important criterion in the diagnostic classification of crystal deposition diseases.

While polarized light microscopy has been used to identify most monosodium urate (MSU) and CPPD crystals in joint fluids, it does not detect the minute size (0.7-2 µM in length) crystals, e.g., BCP. The identification of these crystal typically requires the use of scanning electron microscopy (SEM), transmission electron microscopy (TEM), atomic force microscopy, and Fourier transform Infrared (FTIR) analysis. However, these instrumentations are not readily available, are time consuming to operate, require expert personnel for operation, and are generally expensive to use for most clinical diagnosis.

A semi-quantitative technique employing $^{14}C$ ethane-1 hydroxy 1,1 diphosphonate (EHDP) binding and an Alizarin Red S Staining procedure had reportedly been used to identify minute calcium-containing crystals in joint fluids. Although these procedures are both relative easy to perform in a clinical laboratory setting, their use is limited. For example, the use of the $^{14}C$-EHDP binding assay has been reported only to identify BCP crystals, and $^{14}C$-EHDP is not available commercially. While the Alizarin Red staining procedure can be used as a screening test to detect calcium compounds, it does not give quantitative measurement or identification of individual species of calcium-containing crystals, which is problematic since synovial fluids often contain more than one species of crystals. For example, synovial fluids containing CPPD crystals more often than not also contain BCP crystals. These and other shortcomings are important, and significantly limit the use of such methods.

1. Assays

A key aspect of the invention concerns assay methods to one or more detect disease-associated crystal species in a biological sample, such as a sample of synovial fluid drawn from an articular joint of a subject, preferably a mammalian patient, particular a human patient. Disease-associated crystal species include such species as crystallized basic calcium phosphate (e.g., carbonate-substituted apatite, octacalcium phosphate, and tricalcium phosphate), crystallized calcium pyrophosphate dihydrate, crystallized magnesium-substituted tricalcium phosphate, and crystallized calcium oxalate, as well as combinations of such crystal species. Calcium-containing crystal species are implicated in various diseases, including osteoarthritis (OA), pseudogout, and acute calcific periarthritis.

In general, such methods involve contacting the sample with an excess of a detectable crystal-tagging compound in order to drive the reaction kinetics to favor complete binding of the crystal species with which the tagging compound reacts. The resulting tagged crystal species complexes are then preferably separated from unreacted tagging compound molecules, preferably to help reduce background. The tagged crystal species complexes can then be detected, if desired.

Preferred detectable crystal-tagging compounds are those that comprise a crystal reactive compound, such as an anti-mineralization compound like phosphocitrate, which reacts with calcium-containing crystals, and a detectable label. Preferred labeling moieties (i.e., "labels") include radiolabels (e.g., $^{111}In$, $^{99}Tc$, $^{14}C$, $^{131}I$, $^{125}I$, $^{3}H$, $^{32}P$, or $^{35}S$), fluorescent labels (e.g., rare earth chelates (europium chelates), fluorescein and its derivatives, rhodamine and its derivatives, dansyl, Lissamine, phycoerythrin and Texas Red), chemiluminescent labels, and members of high affinity binding pairs (e.g., antibody-antigen, receptor-ligand, biotin-avidin, etc.). Radiolabels can be detected using any suitable method, including scintillation counting. Fluorescence can be quantified using a fluorimeter. Chemiluminescent substrates become electronically excited by a chemical reaction and may then emit light that can be measured (using a chemiluminometer, for example) or donates energy to a fluorescent acceptor.

Various enzyme-substrate labels are also available and known in the art. The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like.

Sometimes, the label is indirectly conjugated to the tagging compound. The skilled artisan will be aware of various techniques for achieving this. For example, the label can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of a label, the tagging compound is conjugated with a small hapten (e.g., digoxin)

and one of the different types of labels mentioned above is conjugated with an anti-hapten antibody (e.g., anti-digoxin antibody). Thus, indirect conjugation of the label can be achieved. Of course, other indirect types of conjugation may be used.

In preferred embodiments, some, but not all, crystal species within the tagged crystal species complexes are degraded so as to solubilize at least a portion of the label moiety, the detection of which can be used to determine whether a particular disease-associated crystal species is present in the sample. Such selective degradation can be performed using any suitable chemical, enzymatic, or physical process. In the context of disease-associated crystallized calcium species, enzymatic degradation mediated by a pyrophosphorylase is preferred, as it degrades some, but not all, crystallized calcium species that may be present in a particular biological sample.

Following release of the soluble label, measurement of the label in the soluble fraction and/or insoluble fractions can be compared with standard curves to determine the amount of one or more crystallized calcium species present in the sample.

2. Kits

The kits of the invention comprise at least one of the reagents needed to perform the particular assay packaged in a suitable container for storage and transport. Instructions for performing the assay are preferably also included.

In general, the kits of the invention include at least the detectable crystal-tagging compound needed to perform one or more desired assays. Tagging compound may be supplied in any suitable form, including dry (e.g., lyophilized) or liquid, stored in a suitable container. For assays that involve chemical or enzymatic degradation of one or more particular disease-associated crystal species, the kit preferably also includes those reagents stored in a separate container and appropriately formulated.

3. Devices

The invention also concerns devices configured for performing one or more assays according to the invention, alone or in conjunction with other assays. Preferably, such devices are configured to rapidly perform one or more competitive or sandwich immunoassays in a point-of-care or clinical diagnostic laboratory.

To perform immunoassays, antibodies reactive with an assay component are necessary. Antibodies, or antibody fragments or derivatives, can be prepared by any suitable process. Polyclonal or monoclonal antibodies can be used. Suitable antibodies can be developed using procedures known in the art. See, e.g., Antibodies, A Laboratory Manual, Cold Spring Harbor Laboratory, Ed Harlow and David Lane (1988). Preferred antibodies are those which bind the desired antigen with a $K_d$ value of no more than about $1 \times 10^{-7}$ M; preferably no more than about $1 \times 10^{-8}$ M; and most preferably no more than about $5 \times 10^{-9}$ M.

Antibodies may be employed in any known assay method, such as competitive binding assays, direct and indirect sandwich assays, and immunoprecipitation assays.

Competitive binding assays rely on the ability of a labeled standard to compete with the test sample analyte for binding with a limited amount of antibody. The amount of target in the test sample is inversely proportional to the amount of standard that becomes bound to the antibodies. To facilitate determining the amount of standard that becomes bound, the antibodies generally are insoluble before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the analyte to be detected. In a sandwich assay, the test sample analyte typically is bound by a first antibody that is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

4. Applications

The assays of the invention have many applications, preferred examples of which include assays for diagnostic purposes, including to monitor disease progression and therapeutic efficacy. Depending upon the particular application, the assay can performed in a qualitative, semi-quantitative, or quantitative manner.

EXAMPLES

The invention will be better understood by reference to the following Examples, each of which merely illustrates a particularly preferred embodiment for practicing the invention. None of them is to be considered limiting.

Example 1

Quantification of Calcium-Containing Crystals in Solution

This example describes a new, rapid in vitro method to quantify the amount of insoluble calcium salt crystals in a solution known or suspected to contain such crystals. This assay involves the detection of $^{14}$C-labeled phosphocitrate ($^{14}$C-PC). PC is an anti-mineralization compound found in mitochondria, and it binds specifically and quantitatively to all calcium-containing crystal species. This method uses a combination of binding of $^{14}$C-PC to a mixed population of calcium crystal species followed by specific enzyme digestion. To quantitate the amount of calcium crystals present in solution, standard curves for PC binding to calcium crystal species such as BCP and CPPD are used. The protocol is described in detail in the following paragraphs of this example.

This example considers the circumstance of a solution containing BCP and CPPD crystals. To determine the concentration of each of the crystal species, a standard curve for each is prepared to show PC binding to 0-100 ug of BCP crystals and 0-100 ug of CPPD crystals. The results of the following assay can then be plotted on these curves to determine the concentration of each these two crystal species in solution.

The assay is conducted by preparing two sets of triplicate preparations of mixed BCP and CPPD crystals plus known amount of $^{14}$C-PC (preferably in vast excess to drive the reaction kinetics in favor of complex formation). After incubating the solutions (e.g., for 15-30 min.) and performing a trypsin digestion (2 mg/ml in physiological buffered saline) for 30 minutes, $^{14}$C-PC:crystal complexes are isolated by centrifugation (1,000 g). Radioactivity in the pelleted material represents the total amount of calcium crystals present in the initial mixture. The pellets can be washed, for example, by using with $dH_2O$, after which they are resuspended. In one set of triplicate samples, the pellets are dissolved in 100 ul of 2 mM EDTA in water. Dissolved mineral containing ($^{14}$C) is then diluted in 100 ul $dH_2O$, and radioactivity representing total BCP and CPPD crystals in the original solution can be counted. The pellets in the other set of triplicate samples is treated for 1 hr at 37° C. with 1 ml of baker's yeast pyrophosphatase (PPiase) (prepared fresh as a 2 u/ml (units per milliliter) solution in Hank's Balanced Salt Solution containing 0.5 mMMgCl$_2$ and 0.4 mMMgSO$_4$). The PPiase-treated samples are then centrifuged at 1000 g for 15 min. and the supernatents analyzed for $^{14}C$ radioactivity. Since PP$_i$ase specifically solubilizes CPPD crystals, the amount of radioactivity in the supernatant represents CPPD crystals, which can be determined as the difference between the total radioactivity in the samples that are not digested with PP$_i$ase and the amount of radioactivity in the supernatant of the samples digested with PPiase. Sample number in each of the assay can vary, and any suitable statistical analysis tools can be used, for example, the Wilcox on rank sum test, to compare paired samples.

Example 2

Detection and Quantification of Calcium-Containing Crystals in Synovial Joint Fluid This example describes a new, rapid in vitro method to measure the concentration and the identify the types of insoluble calcium salt crystals in joint fluids. It can be used both to diagnose disease as well as to gauge disease progress in patients under treatment.

This assay involves the detection of phosphocitrate. PC is an anti-mineralization compound found in mammalian mitochondria. Phosphocitrate binds specifically and quantitatively to all calcium-containing crystal species. This method uses a combination of binding of calcium crystals with $^{14}C$-labeled PC and specific enzyme digestion.

To determine whether a patient's joint fluid contained a mixed population of BCP and CPPD crystals, synovial fluid is first treated with a known amount of $^{14}C$-labeled PC for 15 min. The reaction is then centrifuged at 5,000 g for 10 min. to collect the labeled crystals from the fluid. Crystals are then digested with one ml of 10 units of bakers yeast pyrophosphatase (PP$_i$ase) in Hank's Balanced Salt solution containing 0.5 mM MgCl$_2$ and 0.4 mM MgSO$_4$ for 1 h at 37° C. This reaction is then centrifuged for 5 min. Since PP$_i$ase specifically solubilizes CPPD crystals, the free radioactivity in the supernatant is from CPPD and the non-solubilized crystals are BCP crystals. From standard binding curves of $^{14}C$-labeled PC to BCP and CPPD, one can determine the amount of each species of crystal in the patient's joint fluid.

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of assaying for crystallized calcium pyrophosphate dihydrate (CPPD) in a biological sample, comprising:
   (i) contacting a biological sample from a patient with an excess of a detectable calcium crystal-tagging compound reactive with a plurality of crystallized calcium species under conditions that allow the detectable calcium crystal-tagging compound to react with any crystallized calcium species present in the biological sample to form detectable crystallized calcium complexes, wherein the detectable calcium crystal-tagging compound is radiolabeled phosphocitrate;
   (ii) removing substantially all unreacted detectable calcium crystal-tagging compound;
   (iii) contacting the detectable crystallized calcium complexes with a reagent that selectively degrades CPPD to release a soluble detectable species, wherein (x) the reagent that selectively degrades CPPD is a pyrophosphorylase or pyrophosphatase and (y) the soluble detectable species is dissolved mineral containing the radiolabel; and
   (iv) detecting the soluble detectable species, thereby detecting the presence of CPPD in the biological sample.

2. A method according to claim 1, wherein the biological sample is a fluid sample.

3. A method according to claim 2, wherein the fluid sample is a sample of synovial fluid.

4. A method according to claim 1, wherein the detection step is qualitative, semi-quantitative, or quantitative.

5. A method according to claim 1, wherein the reagent that selectively degrades CPPD to release a soluble detectable species is a pyrophosphorylase.

6. A method according to claim 1, wherein the radiolabel is selected from the group consisting of $^{111}In$, $^{99}Tc$, $^{14}C$, $^{131}I$, $^{125}I$, $^{3}H$, $^{32}P$, and $^{35}S$.

* * * * *